FLOWERING AND FRUITING PEACH TREE
Filed Nov. 20, 1950 2 SHEETS--SHEET 1
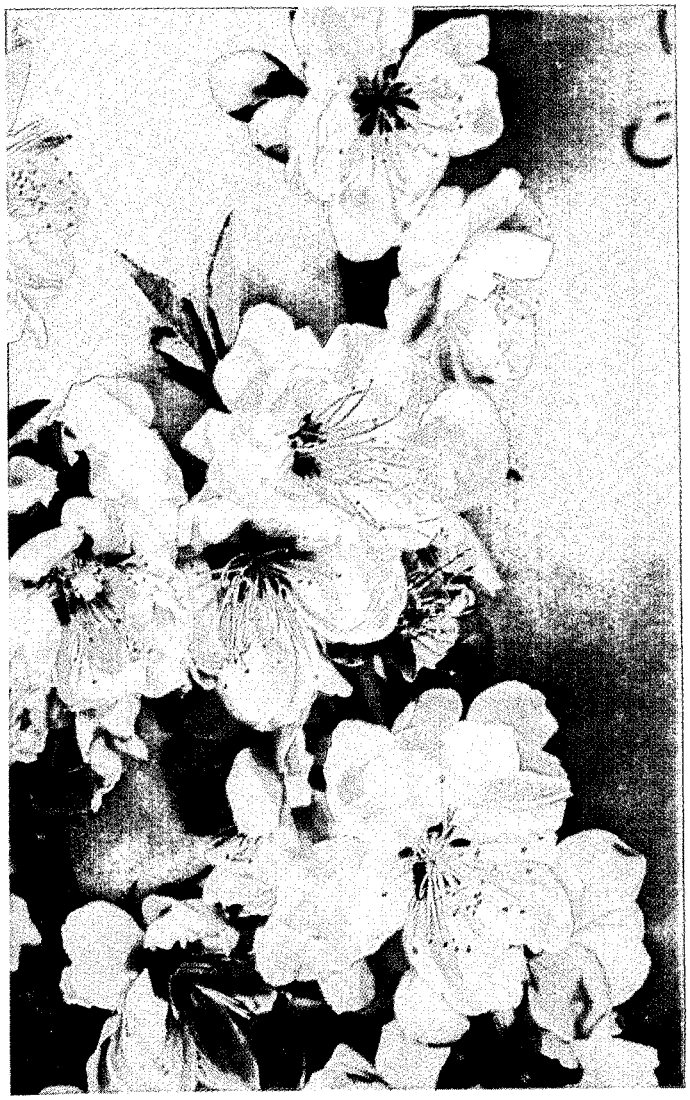
Inventor.
W. E. Lammerts
By: Robb & Robb
attorneys.

FLOWERING AND FRUITING PEACH TREE
Filed Nov. 20, 1950 2 SHEETS—SHEET 2
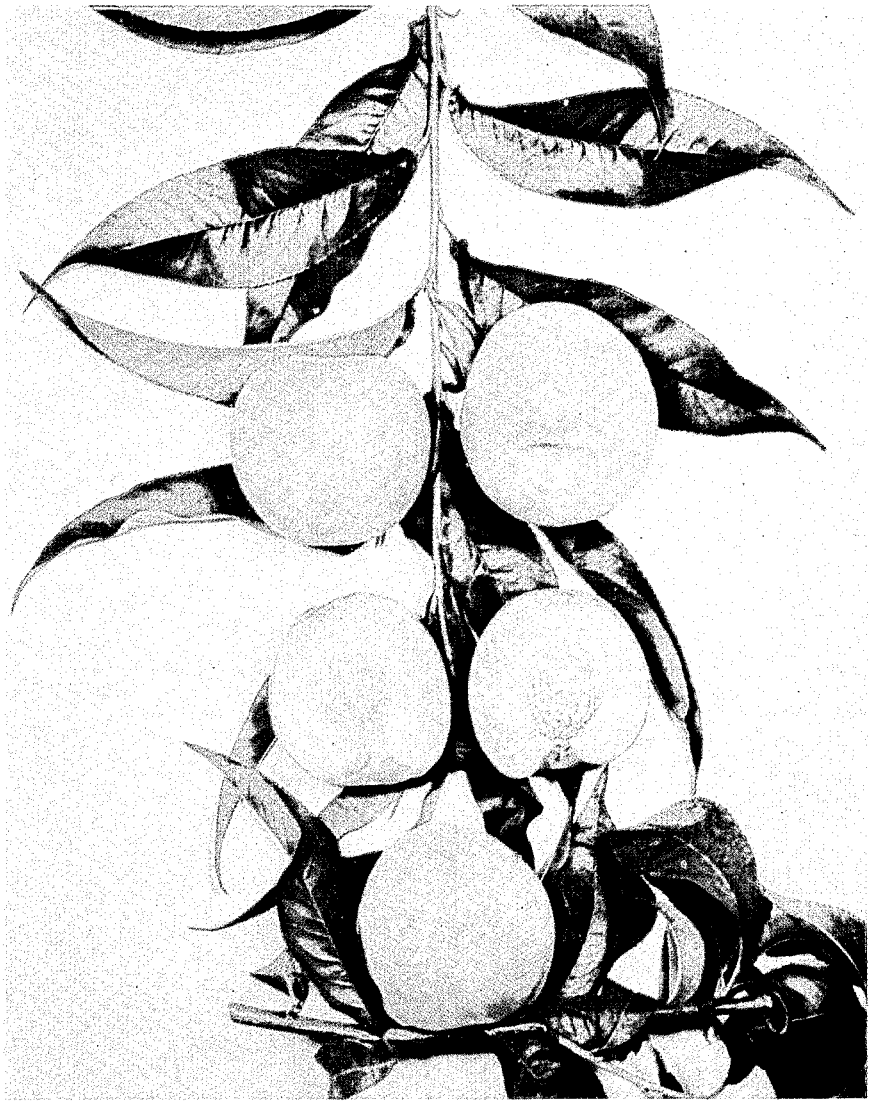
Inventor.
W. E. Lammerts
By: Robbins Robb
Attorneys.

Patented May 6, 1952

Plant Pat. 1,093

UNITED STATES PATENT OFFICE 1,093

FLOWERING AND FRUITING PEACH TREE

Walter E. Lammerts, La Canada, Calif., assignor to Descanso Distributors, Inc., La Canada, Calif., a corporation of California Application November 20, 1950, Serial No. 196,637

1 Claim. (Cl. 47—62)

The present invention appertains to a new and distinct variety of flowering and fruiting peach tree, originated as a seedling derived by crossing an unnamed and unpatented early-ripening hybrid obtained by crossing a selected hybrid of "Chinese Dwarf Evergreen" (unpatented) × "Rio Oso Gem" (Plant Patent No. 84) with a selected hybrid of "Babcock" (unpatented) × "Mayflower" (unpatented) and an unnamed and unpatented double-flowering seedling obtained by growing seed from open-pollinated fruit of "Chinese Dwarf Evergreen" (unpatented) × "Rio Oso Gem" (Plant Patent No. 84).

The above noted breeding has produced a peach tree having a unique combination of characteristics unlike its parents or any other known variety of which I am aware.

One of the most significant and outstanding characteristics of this new variety is its abundant production of very large, highly ornamental, double flowers having from 15 to 18 large petals of predominantly light pink color.

Another outstanding and important characteristic of the new variety is its production of fruit resembling that of the variety "Robin" (Plant Patent No. 529) in respect to the coloration of the fruit and its general shape and appearance, but averaging larger in size and ripening about a week to ten days later than "Robin." In further contrast, with "Robin," the fruit of the new variety is almost completely freestone and has relatively little red coloring in the flesh except right next to the skin on the side which is exposed to the sun.

The new variety is still further characterized by being more vigorous than the variety "Robin" and has a significantly shorter chilling requirement which makes it especially adapted to warm winter climates where it is useful as a home-use tree by combining highly ornamental, and early-flowering qualities with good production of early-ripening, edible fruit of good keeping and shipping qualities. Following very warm winters, the new variety leafs out late in January and usually begins to flower during the last week of January, but following cold winters, it remains dormant and does not begin flowering until about the middle of February, whereas the variety "Robin" usually does not begin to flower until late February or early March.

Asexual reproduction of this new variety by budding near McFarland, California, shows that the foregoing characteristics come true to form and are established and transmitted through succeeding propagations.

The accompanying drawings show specimens of the flowers, fruit and foliage of the new variety, the fruit being shown in both elevation and in plan, as well as in section both with and without the stone.

The following is a detailed description of the new variety, based upon observations of specimens grown at La Canada, California, with color terminology in accordance with British Royal Horticultural Color Standards, except where general color terms of ordinary dictionary significance are obvious:

Dates first and last picking: June 12–20.

Tree: Large; vigorous; upright; open; vase-formed; very productive; regular bearer.

*Trunk.*—Medium stocky; medium smooth.

*Branches.*—Medium stocky; medium smooth; color near maroon Plate 1030 above and near Scheeles green Plate 860/1 lower surface; glossy. Lenticels — numerous; small.

*Leaves.*—Length—3¾ to 5 inches. Width—1¼ to 1½ inches. Medium size; acuminate to lanceolate; medium thickness; near Parsley green Plate 00962; mid rib strongly tinged with anthocyanin pigment; smooth. Margin—finely serrate. Petiole-medium length; medium thickness. Glands—average number—1 or 2. Opposite; small; globose; green; position immediately below leaf blade at upper part of petiole. Stipules—very small, practically absent.

Flowers: Flower Buds—Large; long; obtuse; plump; free; slightly pubescent.

*Flowers.*—Dates first and full bloom—January 26th; full bloom February 14th. Early compared with other varieties. Size—large. A distinguishing feature of this new variety is the large number of very large flowers 2 inches in diameter having 15 to 18 large petals, making very showy ornamental appearance in the early spring. Color—older flowers and margins of petal Rose Pink, Plate 427/3, shading to Rhodamine Pink, Plate 527/3, at edges of freshly opened petals; predominantly Rhodamine Pink, Plate 527/2, shading to Phlox Pink, Plate 625/2, toward base of petal, and actual base of petal Spirea Red, Plate 025/1.

Fruit: Maturity when described—Eating ripe. Date June 10–15.

*Size.*—Uniform; medium. Diameter axial—2⅛ to 2¼ inches. Transverse in suture plane—2¼ to 2⅜ inches. At right angles to suture plane—2¼ to 2½ inches.

*Form.*—Uniform; usually symmetrical to slightly unsymmetrical; globose to broadly ovoid.

*Suture.*—Distinct; extends from base to apex.

*Ventral surface.*—Strongly lipped toward base throughout both sides. Lips—slightly unequal.

*Cavity.*—Rounded; elongated in suture plane with suture showing on both sides. Depth—¼ inch. Breadth—¾ inch.

*Base.*—Rounded.

*Apex.*—Rounded. Pistil point—Apical.

*Stem.*—Length—¼ inch; medium stout; glabrous. Adherence to stone—medium strength.

*Skin.*—Medium thickness; medium tender; semi-free. Tendency to crack—none in dry season. Color—small patches of Chartreuse Green, Plate 663/1, near base diffusing into Scarlet, Plate 19/2, striped and specked with Current Red, Plate 821/3, to Oxblood Red, Plate 00823, on sun-exposed portions. Down—scant; short; rolls up when rubbed.

*Flesh.*—Color—white with greenish tinge; mottled with red on sunny side. Surface of pit cavity—greenish white; few yellow fibres. Amygadalin—scant. Juice—abundant; rich. Texture—firm; fine; crip, to melting. Fibres—few; fine; tender. Ripens—even. Aroma—pronounced. Eating quality—good.

*Stone.*—Free; parts from flesh smoothly; sometimes retains short fibre-like threads along ridges. Size—medium; length 1¼ to 1⅜ inches; breadth ¾ to ⅞ inch; thickness ⅝ to ¾ inch. Form—ovoid; cuneate toward base; pointed. Base—oblique. Hilum—narrow; oblong. Apex— acute. Sides—unequal; curved on right and left sides. Surface—irregularly furrowed throughout; ridged near base; pitted throughout but not deeply. Ridges—jagged toward base. Pits—circular and elongated. Ventral edge—thin with wing toward base. Dorsal Edge—narrow with narrow groove toward base. Color—commonly called Buff-Yellow or near Maize Yellow, Plate 607/3. Tendency to split—slight in dry season.

Use: Market; local; dessert.

Keeping quality: Good.

Resistance to: Diseases—good resistance to *Exoascus deformans* (peach leaf curl), as determined by observation and comparison with standard peach varieties grown under comparable conditions and which ordinarily require spraying each spring under conditions prevailing at La Canada, California, whereas my new variety has not required spraying.

Shipping quality: Good.

I claim:

A new and distinct variety of ornamental and fruiting peach tree, characterized as to novelty by its early production of large, many-petalled, highly ornamental flowers of predominantly light pink color, by its production of relatively early-ripening, large, edible, freestone fruit of good keeping and shipping qualities, resembling that of the variety "Robin" (Pl. Pat. No. 529) in respect to the coloration of the fruit and its general shape and appearance, but ripening somewhat later and having less red coloring in the flesh, and by its vigorous habit of growth and shorter chilling requirement suitable to warm winter climates, substantially as shown and described herein.

WALTER E. LAMMERTS.

No references cited.